United States Patent [19]

Sorbini

[11] Patent Number: 4,576,932

[45] Date of Patent: Mar. 18, 1986

[54] DIETARY SUPPLEMENT AND METHOD

[75] Inventor: Paolo Sorbini, Milan, Italy

[73] Assignee: Also Laboratori S.A.S., Italy

[21] Appl. No.: 457,156

[22] Filed: Jan. 11, 1983

[51] Int. Cl.$^4$ ........................................... A61K 31/715
[52] U.S. Cl. ........................................ 514/54; 514/23
[58] Field of Search .......................... 424/180; 514/23

[56] References Cited

U.S. PATENT DOCUMENTS

| | | | |
|---|---|---|---|
| 2,774,710 | 12/1956 | Thompson et al. | 424/180 |
| 2,935,408 | 5/1960 | Steinitz | 424/180 |
| 4,230,695 | 10/1980 | Ecker | 424/180 |
| 4,251,550 | 2/1981 | Proctor | 426/72 |

FOREIGN PATENT DOCUMENTS

| | | |
|---|---|---|
| 1041600 | 3/1964 | United Kingdom . |
| 1106882 | 6/1966 | United Kingdom . |

OTHER PUBLICATIONS

Kay, R. M., *Journal of Lipid Research*, vol. 23, No. 2, Feb. 1982, 221–242.

Williams, et al., *The Lancet*, Feb. 3, 1979, vol. 1, No. 8110, 271–272, "Fibre and Diabetes".

Jenkins, et al., *British Medical Journal*, May 27, 1978, vol. 1, No. 6124, 1392–1394, "Dietary Fibres, Fiber Anal. . . . ".

Blackburn, et al., *Gastroenterology*, vol. 82, No. 4, p. 821, 1982, "More on Dietary Fiber and Carbohydrate Metabolism".

Rain, et al., The Journal of the Association of Physicians of India, vol. 29, Sep. 1981, 741–743.

Jenkins, et al., *The American Journal of Clinical Nutrition*, Jan. 1979, pp. 16–18, "Dietary Fiber and Blood Lipids . . . ".

Jenkins, et al., *The Lancet*, Feb. 24, 1979, vol. 1, No. 8113, pp. 434–435, "Fiber and Diabetes".

Kritchevsky D., *Lipids*, vol. 13, No. 12, 1978, pp. 982–985, "Influence of Dietary Fiber on Bile and Metabolism".

Taylor, et al., Gastroenterology, vol. 76, No. 5, Part 2, 1979, "80th Annual Meeting of the Amer. Gastroenterological Association".

Rabbi, A., *Alim. Nutr. Metab.*, 3:105–110, (1982), "Significato Della Dieta Iperprot. Nella Dietot. Dell-'Obesita".

Howard, et al., *Alim. Nutr. Metab.*, 3:111–119, (1982), "Physiopath. of Protein Met. in Rel. to Very Low Cal. Regimes".

Audigier, J. C., *Med. Chir. Dir.*, vol. 8, pp. 215–217, (1979), "Fibres Alimentaires et Lipides Biliaires".

Anderson et al., *The American Journal of Clinical Nutrition*, vol. 32, Jan. 1979, pp. 346–363, "Plant Fiber: Carb. & Lipid Met.".

*Primary Examiner*—Johnnie R. Brown
*Assistant Examiner*—Elli Peselev
*Attorney, Agent, or Firm*—Lerner, David, Littenberg, Krumholz & Mentlik

[57] ABSTRACT

A non-insulin stimulating composition is disclosed comprising fructose, milk protein obtained by ultrafiltration and free from insulin-stimulating substances, and guar gum; said components being present in relation to each other in said composition in amounts by weight of from about 12 to about 54 parts fructose, from about 40 to about 44 parts protein, and from about 0.5 to about 2 grams guar gum per daily dose and a process of using the composition is also disclosed.

7 Claims, 1 Drawing Figure

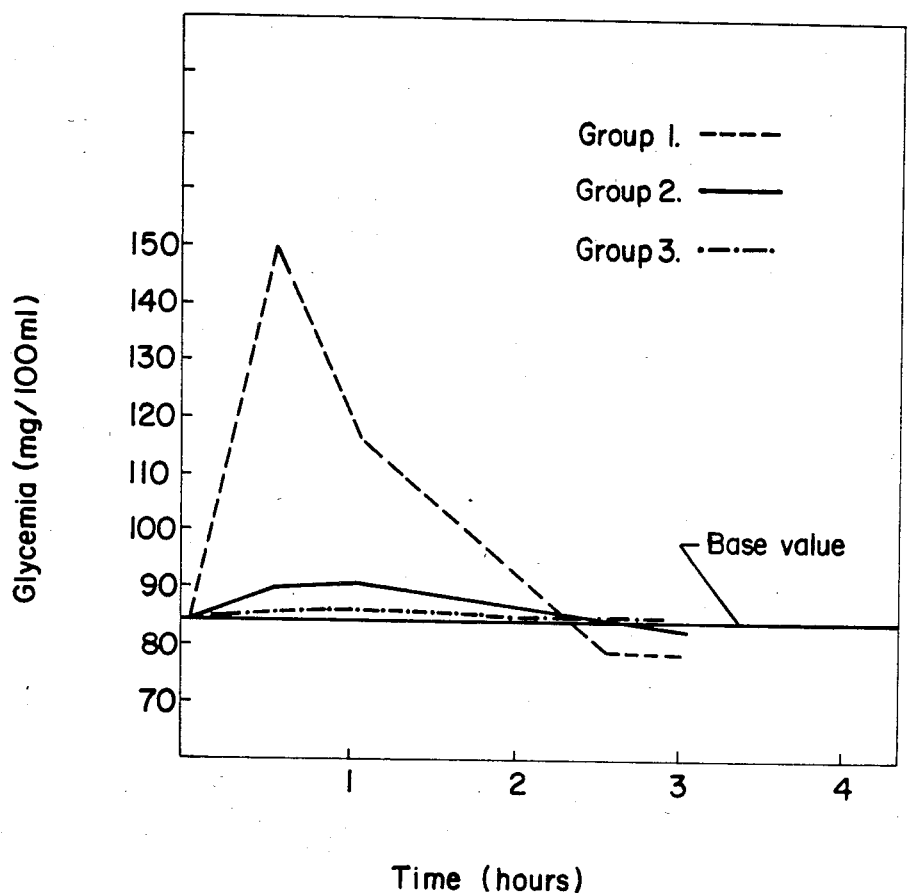

DIETARY SUPPLEMENT AND METHOD

BACKGROUND OF THE INVENTION

The present invention relates to a dietary supplement and a process for using the supplement. The dietary supplement is used to maintain low insulin levels and to help provide body building proteins efficiently to the body.

U.S. Pat. No. 4,230,695 discloses a dietary supplement which includes protein and fructose. However, the compositions disclosed in that patent will not maintain glycemia at about basal levels (see Group 2 in the FIGURE of the present application). Thus, the compositions of that patent will produce an insulin response. Insulin production reduces protein assimilation. Moreover, because increased glucose blood levels produces a "rebound" effect (i.e., the glycemia drops below basal levels), the compositions of the patent produce a subsequent hypoglycemia, so that the subject becomes hungry, reducing the chance that the subject will be able to maintain his diet without additional food intake.

Guar gum is known to provide reduced insulin response with many foods. For example, Jenkins et al. in an article entitled "Dietary Fibres, Fibre Analogues, And Glucose Tolerance: Importance Of Viscosity" in the *British Medical Journal*, Vol. 1, No. 6124, May 27, 1978, pp. 1392–1394, disclose that the addition of guar gum to glucose in a glucose tolerance test reduced blood glucose concentration at one or more points during the test and reduced serum insulin response. However, as pointed out above, it is desirable to provide more than a mere reduction in glycemia and insulin production. Rather, a dietary supplement should ideally maintain glycemia substantially at its basal levels without any "rebound" effect. Also, the dietary supplement should provide a reduced feeling of hunger so that the dieter is not encouraged to eat and therefore can maintain or lower his or her body weight.

SUMMARY OF THE INVENTION

It has now been found that glycemia levels can be maintained at substantially basal levels without a substantial "rebound" effect by employing a dietary supplement comprising fructose, milk protein obtained by ultrafiltration and free from insulin stimulating substances, and guar gum. These components are preferably present in relation to each other in the coomposition in amounts by weight of from about 12 to about 54 parts fructose, from about 40 to about 44 about protein, and from about 0.5 to about 23 grams guar gum for each daily dose. Because the rebound effect is avoided, this dietary supplement alleviates that hunger feelings caused by the hypoglycemia associated with such rebound effect. Moreover, the guar gum in the supplement helps provide the subject with a full stomach feeling and slowly releases the other components into the users intestines so as to avoid substantial insulin response. Furthermore, because of its chemical make up, the dietary supplement of the invention avoids synthesis and accumulation of lipids and favors synthesis of muscle protein components. The dietary supplement is also effective in helping to reduce body weight, especially in subjects having higher quantities of excess fat.

The present invention also contemplates a process in which a subject avoids eating (i.e., fasts from) substantially all insulin stimulating carbohydrates for a period sufficient to reduce the insulin present in the blood stream of the subject to near the basal insulin level. This typically occurs during a fasting period of about two hours. The subject then orally ingests the dietary supplement comprising fructose, milk protein obtained by ultrafiltration and free from insulin-stimulating substances, and guar gum. After such ingestion the subject should avoid further ingestion of insulin stimulating carbohydrates for another period of time, preferably for a time sufficient to obtain the benefits of the ingested composition. The fasting periods help to maintain glycemia at or near the basal levels.

BRIEF DESCRIPTION OF THE DRAWING

The FIGURE is a graphical representation of the glycemia produced in groups of patients treated with aqueous glucose solution, with aqueous fructose solution and with fructose and guar gum in an aqueous solution.

DETAILED DESCRIPTION OF THE INVENTION

The dietary supplement used in accordance with the present invention preferably contains from about 12 to about 54% by weight of fructose. Fructose is a monosaccharide which neither increase glycemia nor insulinemia at dosage levels lower than 50 grams.

Milk protein obtained by ultrafiltration and free from any insulin-stimulating substances is preferably included in the dietary supplement of the invention in amounts by weight of from about 40 to about 44%. Ultrafiltration of milk is conventional. Preferably, the milk protein is extracted from milk which is lipid free and lactose free. Such milk proteins are not denatured but are water soluble. They are neutral in taste and therefore are palatable as a significant portion of a dietary supplement. Moreover, such milk proteins have high nourishment value.

Guar gum is preferably included in the dietary supplement used in accordance with the present invention in amounts of from about 0.5 to about 2 grams per daily dose. Guar gum is a vegetable substance which helps reduce glycemia even when other substances eaten would favor its increase. Chemically, guar gum is a galactomannose, a storage polysaccharide having a molecular weight of about 200,000 derived from a type of Indian bean, with bunches of pods, known by the scientific name of "Cyamopsis Tetragonolobus". The finely crushed endosperm of the seed contained in the pod (known in the trade as guar gum) is used also in the pharmaceutical and food industry because of its excellent binding and absorption properties.

The dietary supplement in accordance with the present invention can also include components to make the composition taste better or to make the composition more healthful. For example, the dietary supplement can include flavorants, preferably natural flavorants, such as vanilla, coffee, apple, tomato, or cocoa flavorants. The dietary supplement can also include added vitamins such as the vitamins of milk. Although preservatives and colorants could be included in the dietary supplement, they are preferably not included in order to maintain the natural composition of the supplement.

The dietary supplement in accordance with the present invention preferably has the following composition:

|                              | % By Weight           |
| ---------------------------- | --------------------- |
| Total Soluble Carbohydrates  | About 35% to about 65% |
| Proteins                     | About 35% to about 40% |
| Moisture                     | Less than about 5.6%   |
| Ash                          | About 2.5% to about 14% |
| Fat                          | About 0.3% to about 3%  |

The components of the dietary supplement of the invention are normally solid powders. Thus, they can be mixed to form the dietary supplement by conventional solid mixing means. The components are typically first dried separately, and then the dried components are mixed by means of a fluid bed granulator. The mixed components can also be formed into tablets by conventional tablet making means.

The dietary supplement of the invention can be prepared for ingestion, for example, by mixing well with water (e.g., stirring in a pitcher or mixing in a blender) in any desired amount. Typically, about 70 grams of the dietary supplement is mixed with 200 ml. or more of water to provide a liquid dietary supplement. If desired, a flavorant such as one of those discussed above can also be included either by mixing it with water or by including it in the dietary supplement itself.

The dietary supplement of the present invention is preferably employed in a process in which a patient first fasts from insulin-stimulating substances for a period of time sufficient to reduce the insulin present in the blood stream of the subject to near the basal insulin level. This period of time is typically about two hours. A dietary supplement comprising fructose, milk protein obtained by ultrafiltration and free from insulin stimulating substances, and guar gum is then orally administered to the subject. After such administration, the subject preferable fasts from insulin-stimulating substances for a further period of time, preferably for a period of time sufficient to obtain the benefits of the dietary supplement. As noted above, the patient will typically ingest about 70 grams of the dietary supplement; however, the amount will vary depending upon the weight and hunger of the patient.

The FIGURE illustrates the advantageous effects obtained with the present invention. Specifically, the FIGURE illustrates the glycemia trend in three groups of patients treated with different sugar solutions. Group 1 was treated orally with an aqueous solution containing 40 grams of glucose. As noted by the graph, after about one-half hour, the gylcemia test had produced a value of about 150 mg./100 ml. Group 2 was treated orally with an aqueous solution containing 40 grams of fructose, and the maximum glycemia level determined was 92 mg./100 ml. For Group 3, the treating solution contained 0.5 grams of guar gum and 40 grams of fructose. In the last case, the graph shows that glycemia was very constant with a peak of 87 mg./100 ml., compared with the 85 mg./100 ml. which was the base value. Thus, the FIGURE demonstrates that those treated with the glucose (Group 1) showed a decrease in glycemia to a value below 80 mg./100 ml. (i.e., below the base value) two and one-half hours after administration. This is the so called "rebound" effect, i.e., the hypoglycemia rebound phenomenon caused by insulinic intervention, which follows a preliminary increase in the glycemic value. The hypoglycemic "rebound" is much lower in Group 2, and is practically unnoticed in Group 3. Moreover, with Group 3 there is little or no rebound effect.

While we do not wish to be bound by any theory, it is thought that the dietary composition of the invention also provides an increase in muscular efficiency. The human body contains stores of lipids and glycides but no stores of protein or amino acids. The proteins contained in foods are split into simple units, amino acids, through enzymatic digestion. Once the amino acids enter the blood stream, they must be used to synthesize the proteins or to obtain sugars or fats for storage purposes, all within the space of a few hours. Thus, to improve muscular strength, power and elasticity, it is necessary for the amino acids to be utilized mainly to "create muscle"; that is to say, they must be made to follow preferentially the proteic synthesis route. However, internal and external factors exist that can favor either the fat or proteic synthesizing route. Training is undoubtedly one such external factor that favors proteic synthesis. An internal factor which can shift amino acids synthesis towards conversion into fat or sugars is a level of insulin in the blood stream higher than base values. Such hyperinsulemia is normally in turn caused by hyperglycemia. In fact, the endocrinous pancreas reacts to an increase of glycemia by producing a higher quantity of insulin in circulation. From the above, it follows that, while it is advisable to associate the intake of noble proteins with training, it is also highly advantageous to decrease glycemia by eating foods that do not produce such effects. From the noble proteins, the organism will be able to draw all of the amine acids needed to synthesize the muscle's fundamental proteins, particularly those that are important from the point view of contraction, namely, actin and myosin.

It would seem that the solution to the problem would therefore be a hyperproteic meal immediately before or a few hours after training, accompanied by water, if necessary. But, proteci synthesis is a process that requires a lot of energy when starting off from amino acids. Therefore, one must supply the organism with noble proteins (taking care not to eat food that can increase glycemia) and substances that can supply ready energy for proteic synthesis itself. The present invention provides such properties. Fructose, an excellent source of energy, does not cause insulin intervention at low dose levels. Moreover, the presence of guar gum in the dietary supplement provides a constant glycemic rate, even in patients who have a latent increase tendency.

The dietary supplement of the present invention has also turned out to be considerably efficacious in reducing body weight. The diencephalic centers of hunger and satisfaction are affected by different stimuli of different origin. Among the factors that can give a feeling of satisfaction, the most important ones are undoubtedly the feeling of gastric replenishment and normoglycemia (i.e., at a base level). The dietary supplement of the present invention produces both of these effects. When the dietary supplement of the present invention is taken at ones normal lunch or dinner time, it immediately induces the feeling of gastric replenishment. Moreover, as discussed above, the supplement also maintains a constant glycemia level for at least a few hours. In addition, hypoglycemia is, as already noted, one of the basic factors in the gensis of hunger. It can arise not only from prolonged fasting, but also following a rich diet of saccharose or sugars which together with digestion gives rise to glucose (see Group 1 of the FIGURE). Because the dietary supplement of the present invention avoids this "rebound", this aspect of hunger is also alleviated.

It is also believed that the dietary supplement of the invention has an effect on adiposity. During the hours following a normal meal (especially if saccharose is included in the food or drink consumed), insulemia tends to rise. High insulemia levels favor the synthesis of fats, i.e., neolipogenesis starting off from amino acids and also simple sugars. On the other hand, if insulin levels remain low (e.g., at base levels), there is a tendency towards lipolisis (hydration of fat), which breaks down the fat into fatty acids and triglycerides.

Due to the mechanism described above, slimming with the dietary supplement of the invention is advantageous. There is no loss in body efficiency. On the contrary, there is a feeling of well-being probably linked to the normoglycemia which can last the whole day. There are no disturbances in digestion or sleep rhythms (patterns), which on the contrary may become easier because of better digestion. Moreover, body tissue does not become flaccid; but rather, body physique remains in tone, even when there is a significant weight loss. In fact, with the dietary supplement of the present invention, as differentiated from some other types of slimming methods which can cause weight loss by protein loss, more fats are lost by use of the present supplement and the level of protein synthesis is raised, if at the same time the subject does physical exercise.

As with most dietary supplements, when used for any protracted period of time, it is recommended that the daily diet of the patient include foods rich in vitamins and mineral salts.

The examples below are intended to illustrate, but not to limit, the present invention.

EXAMPLE 1

A package containing 71 grams of a dietary supplement in accordance with the present invention was prepared by mixing the following components in the indicated amounts:

| COMPONENT | AMOUNT (Grams) |
|---|---|
| Milk proteins obtained by ultrafiltration (minimum titre of protein 85%) | 29.5 |
| Fructose | 41 |
| Guar gum | 0.5 |
| Natural vanilla aroma | 0.2 |

This dietary supplement can be mixed (e.g., in a blender) with about 200 ml. of warm water to provide a liquid dietary supplement for ingestion.

EXAMPLE 2

A cocoa flavored dietary supplement was prepared by mixing the following components in the indicated amounts:

| COMPONENT | AMOUNT (Grams) |
|---|---|
| Milk proteins obtained by ultrafiltration (minimum titre of protein 85%) | 14.75 |
| Fructose | 15 |
| Bitter degreased cocoa | 5 |
| Guar gum | 0.5 |

| COMPONENT | AMOUNT (Grams) |
|---|---|
| Natural cocoa aroma | 0.25 |

This composition can be mixed with water to prepare a cocoa flavored drink.

EXAMPLE 3

A tomato flavored dietary supplement was prepared by mixing the following components in the indicated amounts:

| COMPONENT | AMOUNT (Grams) |
|---|---|
| Milk proteims obtained by ultrafiltration (minimum titre of proteins 85%) | 14.75 |
| Tomato powder | 11 |
| Fructose | 4.25 |
| Sodium chloride | 3 |
| Natural tomato aroma | 2 |
| Guar gum | 0.5 |

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A method for inhibiting an insulin rebound effect in a subject comprising the steps of fasting by said subject from insulin-stimulating carbohydrates for a period to reduce the insulin present in the bloodstream of said subject to near a basal insulin level; orally administering to said subject a dietary supplement, said dietary supplement comprising fructose, milk protein and guar gum, said fructose and guar gum being present in amounts effective to inhibit said insulin rebound effect, and wherein carbohydrates in said dietary supplement consist essentially of substances which do not stimulate insulin production; and fasting by said subject for a period subsequent to said oral administration from insulin-stimulating carbohydrates, said dietary supplement being effective to maintain said insulin present in the bloodstream of said subject near said insulin basal level during said period of fasting, thereby inhibiting said insulin rebound effect.

2. The method according to claim 1 wherein soluble carbohydrates are present in said dietary supplement in a weight ratio to guar gum of from about 12.25:1 to about 91:1 and protein is present in said dietary supplement in a weight ratio to guar gum of from about 12.25:1 to about 56:1.

3. The method according to claim 1 wherein said dietary supplement is a non-insulin stimulating composition comprising a fructose component, a milk protein component free from insulin-stimulating substances, and a guar gum component, said components being present in relation to each other in said composition in amounts by weight of from about 12 to about 54 parts fructose, from about 40 to about 44 parts protein, and from about 0.5 to about 2 grams guar gum per daily dose.

4. The method according to claim 3 wherein said protein is extracted from milk which is lipid free and lactose free.

5. A non-insulin stimulating food supplement composition for inhibiting an insulin rebound effect in a subject during a period which said subject fasts from insulin-stimulating carbohydrates, said composition comprising fructose, milk protein and guar gum, wherein carbohydrates in said composition consist essentially of carbohydrates that do not stimulate insulin production, and wherein soluble carbohydrates are present in said composition in a weight ratio to guar gum of from about 12.25:1 to about 91:1 and protein is present in said composition in a weight ratio to guar gum of from about 12.25:1 to about 56:1, said composition effective to inhibit said insulin rebound effect by maintaining insulin present in the bloodstream of said subject near a basal level during said period of fasting.

6. The composition according to claim 5 wherein said composition is a non-insulin stimulating composition comprising a fructose component, a milk protein component free from insulin-stimulating substances, and a guar gum component, said components being present in relation to each other in said composition in amounts by weight of from about 12 to about 54 parts fructose, from about 40 to about 44 parts protein, and from about 0.5 to about 2 grams guar gum per daily dose.

7. The composition according to claim 5 wherein said protein is extracted from milk which is lipid free and lactose free.

* * * * *

UNITED STATES PATENT AND TRADEMARK OFFICE
CERTIFICATE OF CORRECTION

PATENT NO. : 4,576,932

DATED : March 18, 1986

INVENTOR(S) : Paolo Sorbini

It is certified that error appears in the above-identified patent and that said Letters Patent is hereby corrected as shown below:

```
Column 1, line 17, "produces" should read --produce--.
Column 1, line 48, "coomposition" should read --composition--.
Column 1, line 50, "about" should read --parts--.
Column 1, line 51, "23" should read --2--.
Column 4, line 32, "amine" should read --amino--.
Column 4, line 39, "proteci" should read --proteic--.
Column 6, line 16, "proteims" should read --proteins--.
```

Signed and Sealed this

Fifteenth Day of July 1986

[SEAL]

Attest:

*Attesting Officer*

DONALD J. QUIGG

*Commissioner of Patents and Trademarks*